United States Patent [19]

Goosen et al.

[11] Patent Number: 4,492,684

[45] Date of Patent: Jan. 8, 1985

[54] SLOW RELEASE INJECTABLE INSULIN COMPOSITION

[75] Inventors: Mattheus F. A. Goosen, Toronto; Anthony M. F. Sun, Willowdale, both of Canada

[73] Assignee: Connaught Laboratories Limited, Willowdale, Canada

[21] Appl. No.: 505,840

[22] Filed: Jun. 20, 1983

[30] Foreign Application Priority Data

Jun. 8, 1983 [CA] Canada .................................. 429960

[51] Int. Cl.³ .......................... A61K 9/22; A61K 9/26; A61K 37/26
[52] U.S. Cl. ....................................... 424/19; 424/22; 424/178
[58] Field of Search ............................ 424/19, 22, 178

[56] References Cited

U.S. PATENT DOCUMENTS

| | | | |
|---|---|---|---|
| 3,551,556 | 12/1970 | Kument et al. | 424/19 |
| 3,937,668 | 2/1976 | Zolle | 424/178 |
| 3,993,071 | 11/1976 | Higuchi et al. | 424/19 |
| 4,349,530 | 9/1982 | Royer | 424/19 |

*Primary Examiner*—Frederick E. Waddell
*Attorney, Agent, or Firm*—Sim & McBurney

[57] ABSTRACT

A slow release injectable insulin composition is provided which is able to control blood sugar levels over extended periods of time. The albumin is partially cross-linked using a concentration of glutaraldehyde which is less than 3.75% v/w of the albumin to form a matrix enclosing the insulin. The composition conveniently is provided in the form of microbeads.

9 Claims, No Drawings

SLOW RELEASE INJECTABLE INSULIN COMPOSITION

FIELD OF INVENTION

The present invention relates to long-lasting injectable insulin compositions.

BACKGROUND TO THE INVENTION

Normoglycemia in diabetic patients is controlled by the injection of insulin into the body of the patient. Insulin injections several times a day are required, although more recently long lasting ultralente and protamine zinc insulin has decreased the frequency of injection for some diabetics to once every day.

There is a need for a system which would permit the administration of one large dose of insulin at widely-spaced intervals of weeks or even months. Such a large dose would need to be associated with some means of permitting the administered insulin to be released into the blood stream over a long period of time, so as to be effective over that period.

It has previously been suggested in European Patent Publication No. 0,054,396, published June 23, 1982, to provide implants, microbeads and microcapsules suitable for injection into an animal body comprising cross-linked but physically-native albumin and a non-albumin substance, such as, a steroid or an enzyme. Upon injection or implantation into an animal body, the non-albumin substance contained therein is released slowly as the cross-linked albumin is slowly dissolved by biodegradation.

Although this prior art publication does not mention insulin as a potential non-albumin substance, superficially this prior art approach would seem promising for the production of long term insulin release. When the cross-linking procedure which is described in the prior art publication using glutaraldehyde, is attempted to be used in conjunction with insulin as the non-albumin substance, the resulting product is ineffective in decreasing blood sugar levels upon injection or implantation in a body.

SUMMARY OF INVENTION

It has now surprisingly been found that there can be produced a biodegradable composition comprising insulin which is able to achieve long lasting release of insulin into the blood stream sufficient to control blood sugar levels upon injection or implantation.

In accordance with the present invention, albumin is partially cross-linked only using less than a critical upper limit of proportion of glutaraldehyde cross-linking agent, namely 3.75% v/w of glutaraldehyde to albumin. By only partially cross-linking the albumin, the insulin which is entrapped within the resulting matrix is able to be released over a period of several weeks to several months and achieve blood sugar level control over that period.

GENERAL DESCRIPTION OF INVENTION

In the present invention, a biodegradable matrix of albumin and insulin is provided. Albumin from any convenient source may be used, including human blood, and is partially cross-linked under relatively mild conditions to form the matrix of albumin in a substantially native form.

Injectable insulin-protein microbeads may be prepared by adding an aqueous suspension, containing protein albumin, insulin crystals and glutaraldehyde cross-linking agent, to a rapidly stirred oil phase to form a water-in-oil emulsion of small water droplets containing protein, insulin and glutaraldehyde in a continuous oil phase. The stirring is stopped once the cross-linking reaction is complete and the resulting microbeads are recovered from the oil phase.

By providing the matrix of cross-linked albumin and insulin in microbead form, administration to the human body is facilitated, since the microbeads are of a size suitable for injection. The matrix however, may be provided in other implantable or injectable forms, such as, pellets or thin sheets.

The most critical parameter of the cross-linking process is the concentration of glutaraldehyde cross-linking agent for the albumin which is used. At a concentration of glutaraldehyde of 3.75% v/w or above, the product which is produced is ineffective in releasing insulin sufficiently to decrease blood sugar levels, whereas at a concentration of glutaraldehyde of less than 3.75% v/w, there is produced a matrix which is effective in permitting sufficient insulin release to achieve a decrease in blood sugar levels. It is noted that the prior art process of European Patent Publication No. 0,054,396 suggests utilization of 5.0% v/w of glutaraldehyde for cross-linking. As indicated above, at such glutaraldehyde concentrations when insulin is used, the product is ineffective in decreasing blood sugar levels.

In the process of the invention, the temperature at which the albumin solution is maintained during and after dispersion of the insulin therein generally does not exceed 37° C. and desirably does not exceed 20° C., and is preferably in the range of 0° to 10° C., most preferably 0° to 5° C. The pH of the albumin solution is preferably maintained in the range of about 5.5 to about 8.5 and most preferably about 7.

To ensure rapid formation of the implants, microcapsules or microbeads, the albumin solution should be relatively concentrated, being at least 10% w/v. However, it is preferred that the concentration of the albumin solution should not exceed about 50% w/v and preferably not exceed 30% w/v.

The process of the invention may be utilized to entrap any desired proportion of insulin, up to about 50 wt% of the matrix. Usually, the proportion of insulin in the product is about 5 to about 40% w/w of the microbeads.

Insulin release from the matrix of partially cross-linked albumin and insulin may be usefully controlled by diffusion or erosion. By increasing the cross-linking density as a result of an increase in the glutaraldehyde concentration, the erosion of the matrix is slower than insulin diffusion, and the rate of insulin release, therefore, declines continuously. If insulin is well immobilized in the solid matrix so that diffusional release is minimal and erosion is relatively fast, the rate of insulin release may be controlled by erosion. This result may be achieved, for example, by utilizing very little cross-linking agent and pre-binding the insulin to another molecule, such as, a stearylated amino acid.

In addition to the product of the invention being biocompatible, inexpensive and versatile, the matrix material has a long shelf life. Insulin-albumin microbeads, for example, may be stored at 4° C. for many months prior to implantation without loss of effectiveness.

EXAMPLES

Example 1

This Example illustrates the preparation of insulin-containing microbeads.

40 mg of beef insulin crystals (23.3 U/mg) were suspended in 0.8 ml of sodium phosphate buffer (1 mM, pH 7.5) containing sodium dodecyl sulfate (1%). 160 mg of bovine serum albumin (BSA) of molecular weight of 67,000 Daltons was dissolved in the suspension which was maintained at 4° C. Cross-linking was initiated by the addition of 0.2 ml of glutaraldehyde solution (2.5% v/v) to provide a final glutaraldehyde concentration of 3.12% v/w of the albumin.

After rapid mixing, the suspension was pipetted into 50 ml of a stirred solution of a corn oil and petroleum ether (1:4 by volume). The water-in-oil emulsion which formed was stirred at room temperature for fifteen minutes. The oil phase was decanted, the microbeads were washed three times with petroleum ether and then dried overnight by weight of in a fume hood. The dry microbeads contained 20% insulin and were stored dry at 4° C.

Example 2

This Example illustrates the effect on blood sugar levels obtained by administration of the insulin microbeads formed by the procedure of Example 1.

(a) Implanatation of Insulin Microbeads:

150 mg dry microbeads produced by the procedure of Example 1 were implanted subcutaneously in the flanks of chemically-induced diabetic rats, by means of a small incision in the skin. The blood insulin levels in the treated rats were monitored over a 21-day period and compared to those for untreated rats. The results are reproduced in the following Table I:

TABLE I

|  | Days | | | | | |
|---|---|---|---|---|---|---|
|  | 0 | 3 | 7 | 10 | 14 | 17 | 21 |
| Blood insulin levels (μU/ml) | | | | | | |
| treated diabetic rats (N = 8) | 14 | 51 | 62 | 75 | 63 | 38 | 21 |
| control diabetic rats (N = 4) | 11 | 6 | 9 | 10 | 6 | 3 | 9 |

As may be seen from the results of Table I, after implantation of the microbeads, the insulin levels gradually increased to reach a maximum at 10 days post-implantation, after which there was a gradual decrease. The blood insulin level remained elevated for up to 3 weeks after implantation, demonstrating the longevity of effectiveness of the product of the invention. There was no significant increase in blood-insulin levels in the control animals.

The blood glucose levels of the same diabetic rats with insulin microbead implants were monitored over the same 21-day period and again compared with the non-treated rats. The results are reproduced in the following Table II:

TABLE II

|  | Days | | | | | | |
|---|---|---|---|---|---|---|---|
|  | 0 | 3 | 7 | 10 | 14 | 17 | 21 |
| Blood sugar levels (mg %) | | | | | | | |
| treated diabetic rats (N = 8) | 370 | 95 | 91 | 84 | 105 | 305 | 380 |
| control diabetic rats (N = 4) | 380 | 390 | 387 | 392 | 400 | 404 | 406 |

As may be seen from the results of the above Table II, after implantation of the microbeads, the blood glucose levels fell from 370 mg percent to 95 mg percent and remained stable for 14 days. By day 21, all the animals were hyperglycemic. The control animals did not display any decrease in their high blood glucose levels.

Body weight changes were also monitored during the test period and in all cases, the treated diabetic rats gained in weight while the control rats did not, as may be seen from the following Table III:

TABLE III

|  | Days | | | | |
|---|---|---|---|---|---|
|  | 0 | 3 | 7 | 10 | 14 |
| Body weight (g) | | | | | |
| treated diabetic rats (N = 8) | 185 | 200 | 210 | 220 | 230 |
| control diabetic rats (N = 4) | 190 | 185 | 180 | 180 | 175 |

(b) Injection of Insulin Microbeads:

40 mg of insulin microbeads were mixed with 2 ml of a glycerol/saline solution containing 75% of glycerol by weight and injected subcutaneously into diabetic rats with a 16-gauge needle. The results obtained were similar to those observed for implanted microbeads.

Example 3

This Example illustrates the effect of the concentration of glutaraldehyde used to cross-link albumin.

The procedure of Example 1 was repeated using varying concentrations of glutaraldehyde from 0.2 to 1.0% v/v and, for the microbeads produced in each experiment, the effective period over which blood glucose levels were decreased was determined. In each case, 150 mg of insulin microbeads were subcutaneously implanted and the results reproduced in the following Table IV are a mean of three tests.

TABLE IV

| Glutaraldehyde v/w albumin | 1.25 | 1.87 | 2.5 | 3.12 | 3.75 | 4.37 | 5.0 | 5.62 | 6.25 |
|---|---|---|---|---|---|---|---|---|---|
| No. of days Blood Glucose levels lowered | 11 | 13 | 13 | 14 | 0 | 0 | 0 | 0 | 0 |

As may be seen from the results of Table IV, at glutaraldehyde concentrations of 3.75% v/w and above, the insulin microbeads are ineffective in producing a decrease in blood sugar levels, whereas sustained blood sugar control is achieved when the cross-linking is effected using lower concentrations.

SUMMARY

In summary of this disclosure, the present invention provides a novel long-acting implantable insulin composition which does not suffer from the drawbacks of

What we claim is:

1. A biodegradable insulin-containing composition suitable for administration to a living body for the control of blood sugar levels therein, comprising a matrix of partially cross-linked physically-native albumin and insulin where the extent of said partial cross-linking is such as to permit insulin to be released from the matrix by diffusion and/or erosion when positioned in the body, said cross-linking being achieved by the use of glutaraldehyde in a concentration of less than 3.75% v/w of the albumin.

2. The composition of claim 1 wherein the concentration of glutaraldehyde is about 1.25 to about 3.12% v/w of the albumin.

3. The composition of claim 1 in the form of injectable microbeads.

4. The composition of claim 1 wherein said insulin comprises about 5 to about 40% w/w of the composition.

5. A method of formation of an insulin-containing biodegradable composition useful for administration to a living body for the control of blood sugar levels therein, which comprises:

forming an aqueous suspension of native albumin, insulin crystals and glutaraldehyde in a concentration of less than 3.75% v/w of the albumin, adding said aqueous suspension to an oil phase under shear to form a water-in-oil emulsion and to cross-link the albumin with said glutaraldehyde to form microbeads of a matrix of partially cross-linked albumin and insulin which permit insulin to be released therefrom by diffusion and/or erosion when positioned in the body, and recovering the microbeads from the oil phase.

6. The method of claim 5 effected at a temperature less than about 20° C.

7. The method of claim 5 wherein the aqueous suspension has a pH of about 5.5 to about 8.5.

8. The method of claim 5 wherein the amount of insulin used provides about 5 to about 40% w/w of the composition.

9. A method of administrating insulin to a human body for the control of blood sugar levels therein, which comprises injecting into the human body an effective quantity of biodegradable microbeads comprising a matrix of partially cross-linked physically-native albumin and insulin wherein the extent of said partial cross-linking is such as to permit insulin to be released by diffusion and/or erosion over an extended period to the body into which the microbeads are injected to achieve said blood sugar control, said cross-linking being achieved by the use of glutaraldehyde in a concentration less than 3.75 v/w of the albumin.

* * * * *